United States Patent [19]
Steiner

[11] 3,948,261
[45] Apr. 6, 1976

[54] UNIT DOSE CONTAINER FOR SURFACE ADMINISTERED VACCINES

[75] Inventor: Dale C. Steiner, Malvern, Pa.

[73] Assignee: American Home Products Corporation, New York, N.Y.

[22] Filed: Nov. 27, 1974

[21] Appl. No.: 527,567

[52] U.S. Cl. ............... 128/253; 128/2 W; 215/227; 215/307; 215/DIG. 3; 206/367
[51] Int. Cl.² ................ A61B 17/20; A61B 10/00
[58] Field of Search ........... 128/253, 329, 333, 2 W; 206/367, 808; 215/227, 307, 355, DIG. 3

[56] References Cited
UNITED STATES PATENTS

| | | | |
|---|---|---|---|
| 3,123,212 | 3/1964 | Taylor et al. | 128/253 X |
| 3,194,237 | 7/1965 | Rubin | 128/253 |
| 3,834,571 | 9/1974 | Bartell | 215/307 X |

FOREIGN PATENTS OR APPLICATIONS

| | | | |
|---|---|---|---|
| 1,309,352 | 10/1962 | France | 128/253 |

*Primary Examiner*—Ronald L. Frinks
*Attorney, Agent, or Firm*—Joseph Martin Weigman

[57] ABSTRACT

The disclosure is directed to a container for unit doses of dry vaccines which are to be administered on the surface of the skin. The unit dose container is made up of a rigid receptacle and a compressible closure which supports a bifurcated needle bearing dried vaccine. The closure is adapted to support the needle in the container during a lyophilizing process while liquid vaccine is dried on the needle. The closure has grooves which in one position of the closure relative to the receptacle permit the vaporized liquid from the vaccine to be withdrawn from the receptacle during lyophilizing. In another position the closure seals the container. The move from the first position to the second position is accomplished merely by pressing on the end of the closure.

1 Claim, 4 Drawing Figures

U.S. Patent April 6, 1976 3,948,261
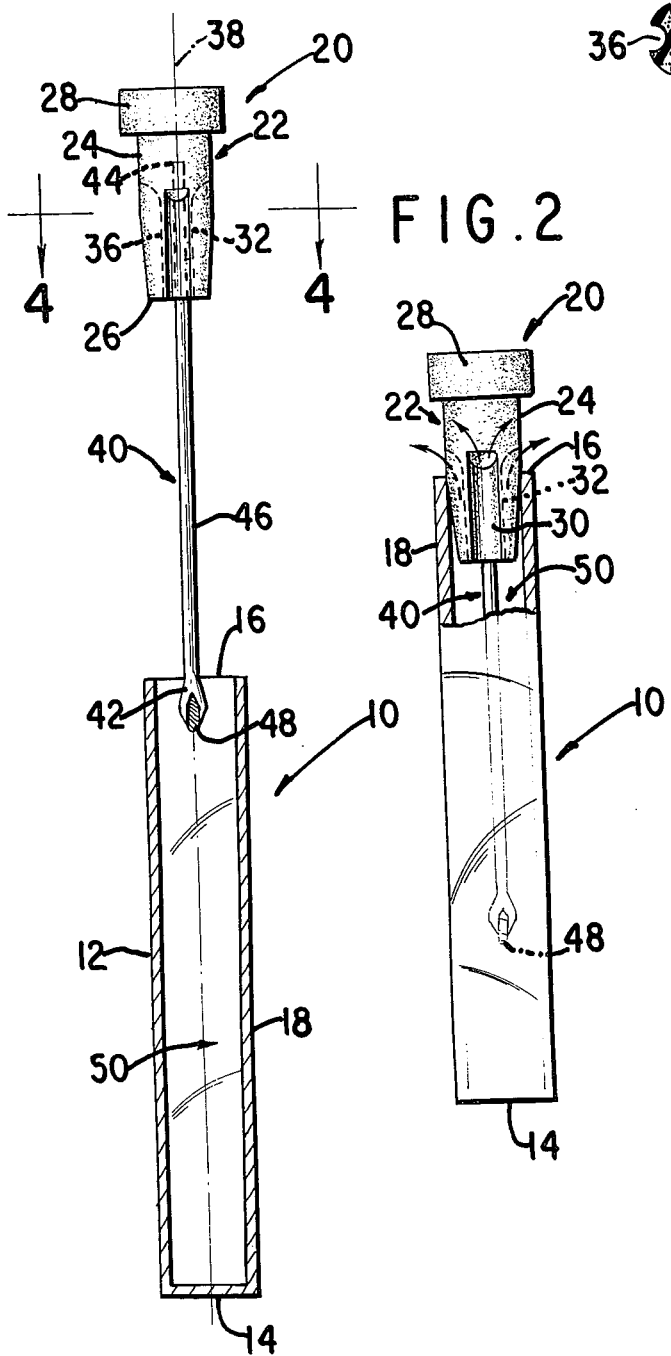
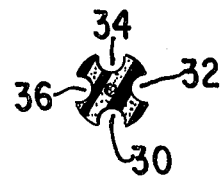
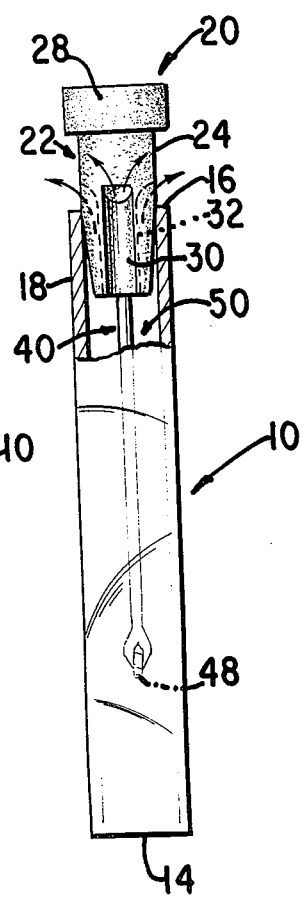
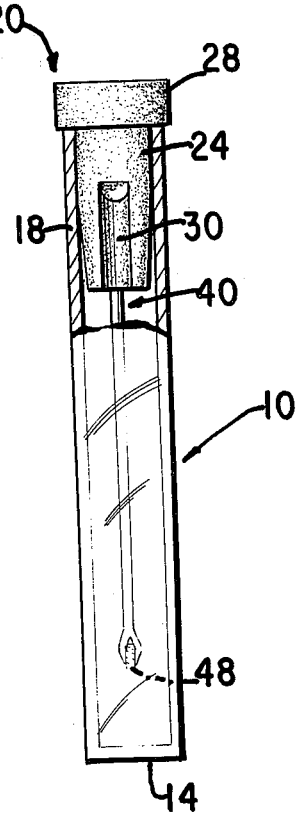

UNIT DOSE CONTAINER FOR SURFACE ADMINISTERED VACCINES

The invention is directed to medical applicator instruments, and more particularly is directed to vaccinating and testing neddles packaged in a unit dose container.

The use of pronged, or bifurcated, vaccinating and testing needles is well known and is described in detail in U.S. Pat. No. 3,194,237, issued July 13, 1965 to Benjamin A. Rubin. The entire contents of that patent are incorporated herein by reference.

Also well known are dispensing containers which will hold a large number of vaccinating needles and will dispense them individually under aseptic conditions. Such containers are described in U.S. Pat. No. 3,212,670, issued Oct. 19, 1965 to Howard Tint and John W. Ridley. Containers for multiple needles are useful where a large number of vaccinations are to be carried out. However, it frequently occurs that a physician is called on to make only one or a few vaccinations at a time. It is uneconomical for him to stock the multiple needle containers which frequently contain 25 or more needles. A single dose container for an individual vaccination is desirable.

Also, it is desirable where a number of units are to be lyophilized at one time that they be open during the lyophilizing process but relatively simply sealable at the conclusion of lyophilization and prior to removal from the lyophilizer.

Accordingly, it is an object of the present invention to provide a single dose container for vaccines which are to be surface administered.

It is another object of the present invention to provide a unit dose container in which a liquid vaccine is retained on a bifurcated needle, lyophilized to a dry condition, and then sealed in the container.

It is a broader object of the present invention to provide a closure for engaging the filling orifices of receptacles for materials which are to be vacuum dried after filling and sealed after drying, in which the sealing may be accomplished while the containers are still in the lyophilizer.

Other and further objects of the invention will be apparent to those skilled in the art from the following description read in conjunction with the drawings in which:

FIG. 1 is an elevational view, partly in section, of a unit dose vaccine container of the invention shown in the open position;

FIG. 2 is an elevational view, partly in section, of the container of the present invention showing the closure lightly engaging the receptacle during lyophilizing;

FIG. 3 is an elevational view, partly in section, of the container of FIG. 1, shown in the closed position after lyophilizing is complete; and FIG. 4 is a cross-sectional view of the closure taken generally along lines 4—4 of FIG. 1.

The object of the present invention may be met with a unit dose container 10 made up of a rigid receptacle 12 closed at one end 14 and having a filling orifice 16 at the opposite end of side wall 18. A closure 20 is made up of a body portion 22 having a diameter at a first end portion 24 which is greater than the diameter of the filling orifice 16. The body portion substantially continuously tapers to a second end portion 26 which has a diameter less than that of the filling orifice 16. A flange 28 is connected to the body portion 22 adjacent to the first end portion 24 and has a diameter greater than that of the first end portion 24. At least one, and preferably a plurality, here shown as four, grooves 30, 32, 34 and 36 are defined longitudinally in the body portion 22, parallel to the longitudal axis 38. Each of the grooves 30, 32, 34 and 36 is preferably of semicircular configuration, as may be seen in FIG. 4, but other configurations may be used. Each of the grooves extends from the second end portion 26 toward the first end portion 24, and passes through and extends on both sides of a transverse plane through the body portion 22, in which the diameter of the body portion is equal to the interior diameter of the orifice 16. The location of that plane is shown substantially along line 4—4 in FIG. 1.

It has been found advantageous that the length of the body portion 22 from first end portion 24 to second end portion 26 be substantially greater, preferably about 50 percent greater, than the diameter of the flange 28. As will further described below, this length tends to guide the closure 20, during insertion and removal from the receptacle 12. The closure is made of a compressible material as is well known in the pharmaceutical arts.

A needle 40 having a bifurcated end 42 is embedded at its opposite end 44 in the body portion 22 to a depth, typically about two-thirds of the body portion, sufficient to firmly engage the closure 20 and needle 40 and support the needle 40, in fixed position. The support end 44 may be of circular cross section as is the middle portion 46 of the needle 40, but advantageous results are obtained if the support end 44 is flattened serving to limit undesirable rotation of the needle 40 relative to the closure 20.

In use, the neddle 40 is dipped into a liquid vaccine causing a droplet 48 of the vaccine to adhere to the needle at its bifurcated end 42. The needle 40 is then lowered into the receptacle 12 until the body portion 22 lightly engages the interior surfaces of the filling orifice 16, as is shown in FIG. 2. In this position the grooves 30, 32, 34, 36 permit communication of the interior 50 with the surrounding atmosphere. With the closure in this position the unit dose container 10 is loaded into a tray or other support and placed into a lyophilizer. There, a vacuum is drawn and the volatile portion of the vaccine solution evaporates and exits through the grooves 30, 32, 34, 36 as shown by the arrows in FIG. 2. When lyophilization is complete the closure 20 is pressed into the receptacle 12 until the flange 28 engages the filling orifice. This is preferably done by mechanical means while the unit dose container is in the lyophilizer. A seal is maintained at that point and also by the engagement of first end portion 24 with the interior surfaces of the wall 18 as may be seen in FIG. 3.

At the place of vaccination the vaccinator removes the closure 20 from the receptacle 12. The length of the body portion 22 serves to guide the needle 40 from the receptacle and prevent accidental contact of the bifurcated end 42 and dried vaccine 48 with the walls 18 of the receptacle 12 and so prevents the accidental removal of the vaccine. The vaccinator then proceeds with vaccination in well known fashion, for instance, by placing a drop of sterile liquid on the skin and scratching the skin under the liquid with the bifurcated end of the needle. The needle, receptacle and the entire unit dose container may then be discarded.

What is claimed is:

1. A container for a unit dose of vaccine which is to be vaccum dried after filling and sealed after drying comprising:
- A. A rigid vial closed at one end and having a filling orifice at the opposite end;
- B. A closure for engaging the interior surface of said filling orifice comprising a compressible material having:
  - i. A substantially circular solid body portion having a first diameter at a first end greater than the diameter of the filling orifice and substantially continuously tapering to a second diameter at a second end having a diameter less than the diameter of said filling orifice;
  - ii. A flange connected to said first end and having a diameter greater than said first end;
  - iii. At least one longitudinal groove defined in the surface of said body portion and extending from said second end to a point intermediate said first and second ends and extending on both sides of a transverse plane of said body portion at which a third diameter is substantially equal to the interior diameter of said filling orifice;
  - iiii. The distance between said first and second ends being greater than the diameter of said filling orifice; and
- C. A bifurcated needle concentrically embedded in the body portion of said closure and extending past said second end, said needle being adapted to support a unit dose of vaccine during filling, drying, sealing and administration; whereby the length of said closure between said first and second ends prevents said needle from contacting the inside of said vial during filling, storage and removal.

\* \* \* \* \*